(12) United States Patent
Ahmad

(10) Patent No.: US 6,612,181 B2
(45) Date of Patent: Sep. 2, 2003

(54) METHOD AND SYSTEM FOR DETERMINING CRACK NUCLEATION OF A PART SUBJECT TO FRETTING FATIGUE

(76) Inventor: Jalees Ahmad, 11772 Sorrento Valley Rd., Suite 145, San Diego, CA (US) 92121-1085

( * ) Notice: Subject to any disclaimer, the term of this patent is extended or adjusted under 35 U.S.C. 154(b) by 0 days.

(21) Appl. No.: 09/945,891

(22) Filed: Sep. 4, 2001

(65) Prior Publication Data

US 2003/0074976 A1 Apr. 24, 2003

(51) Int. Cl.[7] ................................................. G01N 3/32
(52) U.S. Cl. ....................................................... 73/808
(58) Field of Search ........................... 73/808, 809, 810, 73/811, 812, 813, 814, 815, 816, 817, 799, 7, 9; 702/34

(56) References Cited

U.S. PATENT DOCUMENTS 4,336,595 A * 6/1982 Adams et al. ................ 702/34
4,676,110 A * 6/1987 Hodo et al. .................. 73/809
5,883,311 A * 3/1999 Hettiarachchi et al. ...... 73/799
6,467,330 B1 * 10/2002 Vizintin et al. ................. 73/7

* cited by examiner

*Primary Examiner*—Hezron Williams
*Assistant Examiner*—Corey D. Mack
(74) *Attorney, Agent, or Firm*—John R. Ross; John R. Ross, III

(57) ABSTRACT

A method for determining crack nucleation for a part subject to fretting fatigue. Fretting fatigue tests are performed on at least one test specimen having a material composition similar to the part. The results of the test are analyzed to determine a variation of stress intensity factor as a function of time which may be referred to as ($Q\{N\}$) for the test specimen. A relationship is then determined between ($Q\{N\}$) and crack nucleation ($N_i$) for the test specimen. A variation of stress intensity factor as a function of time ($Q\{N\}$) for the part is determined based on the operating conditions and loads of the part. The ($Q\{N\}$) for the part is then corresponded to the ($Q\{N\}$) for the test specimen to determine a crack nucleation value ($N_i$) for the part. In a preferred embodiment, a computer is programmed to conduct the analysis.

28 Claims, 13 Drawing Sheets

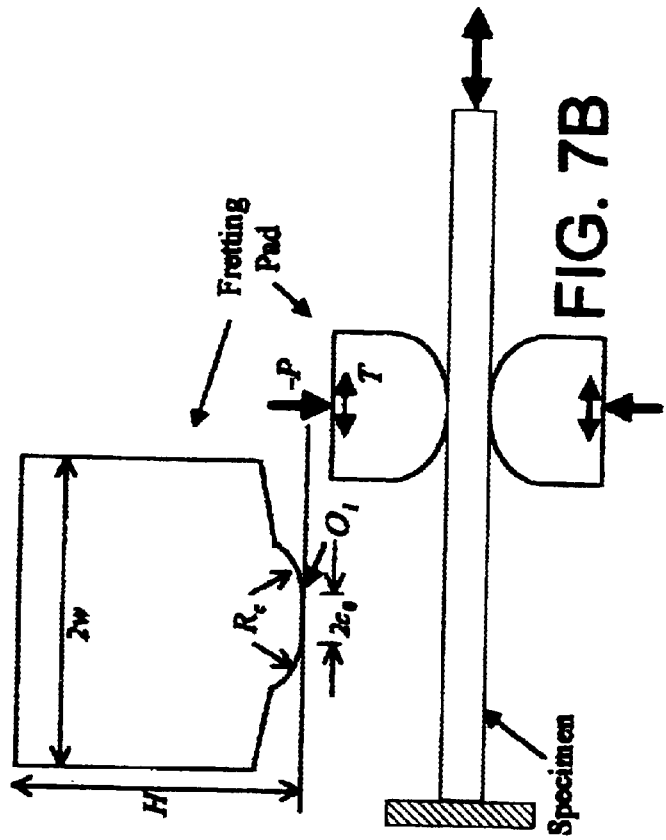
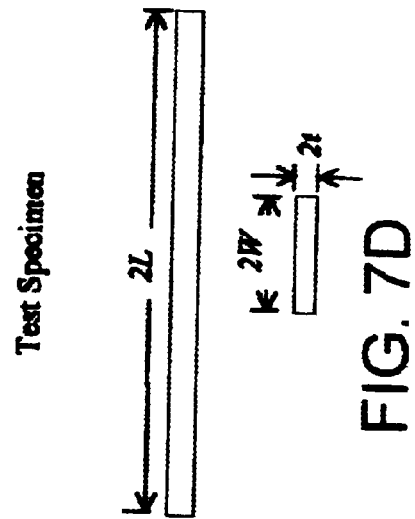
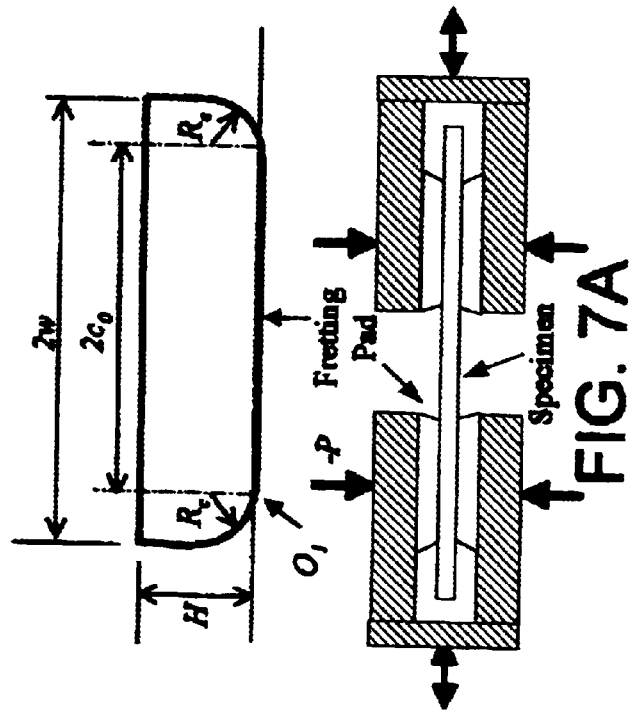
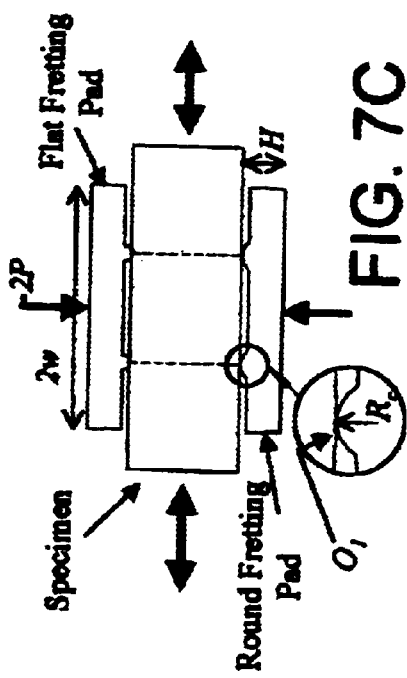
FIG. 7A
FIG. 7B
FIG. 7C
FIG. 7D

METHOD AND SYSTEM FOR DETERMINING CRACK NUCLEATION OF A PART SUBJECT TO FRETTING FATIGUE

The present invention relates to methods for analyzing progressive damage to solid surfaces, and in particular, to damage arising from fretting fatigue.

BACKGROUND OF THE INVENTION

The *ASM Handbook on Friction, Lubrication, and Wear Technology* describes fretting fatigue as the progressive damage to a solid surface that arises from fretting. Fretting is defined as a wear phenomenon occurring between two surfaces having oscillatory relative motion of small amplitude. The phrase crack nucleation, as used in this specification, refers to an operating time period to the occurrence of a crack formation in a part being analyzed or treated. This operating time parameter is typically a number of cycles. The symbol used herein for crack nucleation is ($N_i$).

The first detailed stress analysis of fretting fatigue appears to have been done by Mindlin (see Mindlin, R. D., 1949, "Compliance of Elastic Bodies in Contact", ASME *J. of Appl. Mech.,* Vol. 16, pp 259–268) and remains the predominant basis for addressing a variety of practical problems. In particular, Mindlin's solution has been extensively cited in the literature on fretting fatigue in the context of developing structural life prediction models. Several models have been proposed, each involving one or more parameters assumed related to damage accumulation and failure due to fretting fatigue. Relative efficacies of several such models have been discussed by Szolwinski, et al (see Szolwinski, M. P., Harish, G., McVeigh, P. A., and Farris, T. N., 1999, "Experimental Study of Fatigue Crack Nucleation in Aerospace Alloys with Emphasis on Life Prediction", ASTM STP 1321, Am. Soc. of Test. and Matls.). Some of the proposed models include consideration of stresses near the contact boundary. In these models, generally, the focus is on estimating and using stresses and strains at some fixed distance (d) from the contact boundary. Most models also necessitate assuming a value for coefficient of friction. To some extent, the necessity of choosing d and a constant coefficient of friction reduces objectivity in the application of these models.

What is needed is a better method for analyzing fretting fatigue.

SUMMARY OF THE INVENTION

The present invention provides a method for determining crack nucleation for a part subject to fretting fatigue. Fretting fatigue tests are performed on at least one test specimen having a material composition similar to the part. The results of the test are analyzed to determine a variation of stress intensity factor as a function of time which may be referred to as (Q{N}) for the test specimen. A relationship is then determined between (Q{N}) and crack nucleation ($N_i$) for the test specimen. A variation of stress intensity factor as a function of time (Q{N}) for the part is determined based on the operating conditions and loads of the part. The (Q{N}) for the part is then corresponded to the (Q{N}) for the test specimen to determine a crack nucleation value ($N_i$) for the part. In a preferred embodiment, a computer is programmed to conduct the analysis.

BRIEF DESCRIPTION OF THE DRAWINGS

FIGS. 7A–7D show test configurations of experiments subject to analysis.

DETAILED DESCRIPTION OF THE PREFERRED EMBODIMENTS

Figure 1:
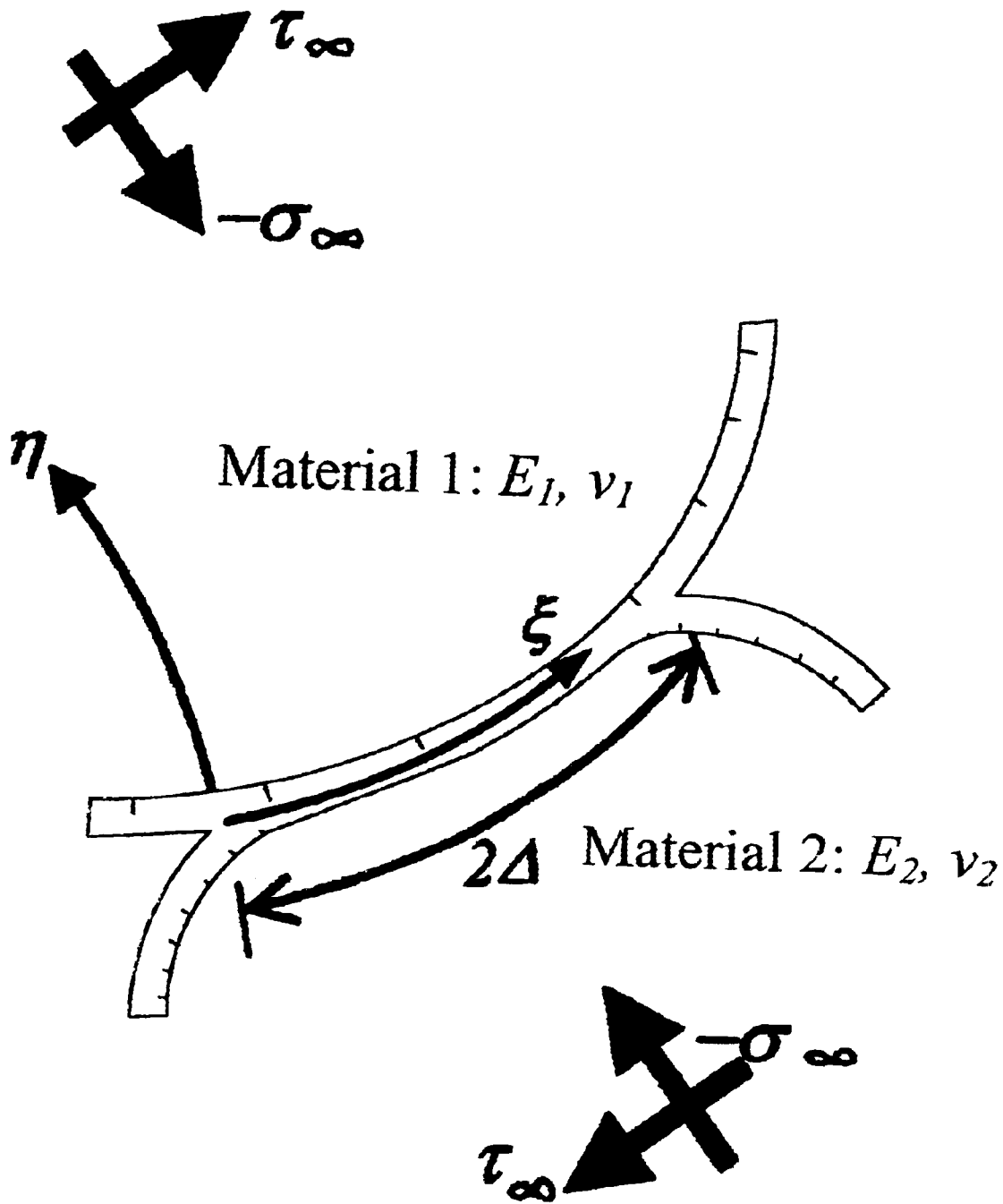
FIG. 1 shows forced contact between two bodies.

In the present invention, a parameter Q has been identified to represent propensity of fretting fatigue damage. Applicant has discovered that fretting fatigue crack nucleation life associated with a given set of material surfaces is uniquely related to the maximum and minimum values of Q occurring in any structural component, device or test sample prone to fretting fatigue. The relationship can be directly applied to life prediction of structural and machine parts and devices, and in design improvements leading to longer part lives. Thus, the discovery can be used to accomplish one or both of the following objectives:

(1) Predict fretting fatigue life (FFL) of an existing part, and (2) Improve design of an existing part to achieve a desired FFL using a Materials Approach, a Mechanics Approach, or a combination of the two approaches.

In a first preferred embodiment of the present invention, the first objective can be achieved by following Steps 1 to 5 described below. Also in a second preferred embodiment, the second objective can be achieved by following Steps 1 to 8.

First Preferred Embodiment

Step 1: Perform fretting fatigue tests in which normal and tangential forces are monitored and the number of cycles (or time) of crack nucleation ($N_i$) and/or of specimen failure ($N_f$) is recorded. The tests are performed under conditions (such as temperature and environment) representative of the operating conditions of the part in actual or anticipated service. Preferred fretting fatigue tests are the Farris, Hutson and Wallace tests described below under the heading "Establishment of Relation Between Q Values and Nucleation Life". Results of those tests are summarized in the manner shown in Table 1 of that section.

Step 2: Analyze each test to determine variation of Q with time (Q{N}) for the specimen throughout the test duration. The analysis is performed using either an exact (closed form) or a numerical mathematical procedure (such as, but not limited to, the finite element method). Q is defined below under the heading "Stress Intensity Factor (Q)". The procedures for determining the variation of Q with time (Q{N}) is discussed below under the heading "Determination of Q Values".

Step 3: Develop a relation (which could be mathematical or graphical) between Q{N} (or a function, A{Q}, thereof) and $N_i$ and/or $N_f$. This step (including the symbols $N_i$ and $N_f$) is described below under the heading "Establishment of Relation Between Q Values and Nucleation Life".

Step 4: Calculate or compute Q{N} for the mechanical component or device (actual or conceptual) under its operating conditions and loads. The calculation/computation is performed using either an exact (closed form) or a numerical mathematical procedure (such as, but not limited to, the finite element method). An example of this step is described below under the heading "Example of Life Prediction".

Step 5: Corresponding to Q{N} found in Step 4, find $N_i$ and/or $N_f$ using the functional relation developed in Step 3. The $N_i$ and/or $N_f$, thus determined, is the predicted FFL of the component or device. This step is also shown under the heading "Example of Life Prediction".

Second Preferred Embodiment

Perform steps 1–5 above.

Step 6: To obtain a desired FFL ($N_D$) by design modifications, use the relation in Step 3 to determine the corresponding desired value of Q or A. Next, affect design modifications and repeat Step 4 until the desired values of Q or A are obtained.

Step 7: To obtain a desired FFL ($N_D$) by material and/or surface modifications, affect modifications with the objective of changing the relation in Step 3 such that, for the same Q found in Step 4, the corresponding $N_i$ or $N_f$ is sufficiently close to $N_D$. With the selected material and/or surface changes, repeat Steps 1, 2 and 3 until the foregoing objective is met.

Step 8: To obtain a desired FFL ($N_D$), use both Step 6 and Step 7 simultaneously or sequentially. Steps 6–8 are discussed in greater detail below under the heading "Example of Design Improvement".

Stress Intensity Factor (Q)

The present work addresses the problem of two deformable solid bodies in forced contact over portions of their surfaces, and acted upon by sliding forces. Of special interest are stresses near the contact boundary, which is particularly prone to nucleation of cracks and other forms of damage. For example, fretting fatigue induced cracks have been found to nucleate near contact boundaries and are of practical concern.

In the present invention, the focus is on analyzing the structure of the singular stress field at the contact boundary. Based on this analysis, a stress intensity factor (Q) is identified. Next, it is found that the maximum and minimum values, $Q_{max}$ and $Q_{min}$, of stress intensity factor are uniquely related to the time or number of load cycles ($N_i$) at crack nucleation due to fretting fatigue.

At a dimensional scale relevant to continuum analysis, surfaces of all bodies in forced contact are mutually tangent everywhere within the contact region, including at the contact boundary. Consider that contact is forced by remote compressive pressure $-\sigma_\infty$ and that bodies are acted upon by forces that result in remote shear stress $\tau_\infty$ (FIG. 1) such that they produce, respectively, only normal and only shear stress in the forced contact region ($\eta=0$, $0 \leq \xi \leq 2\Delta$). The normal stress perpendicular to the contact surface is compressive everywhere except at the contact boundary, where it must approach zero. Of course, depending on shapes, the surfaces of the two bodies can gradually deviate outside the forced contact region.

FIG. 1 is a general depiction of forced contact between bodies of dissimilar materials and shapes. Because the surfaces are tangent at the boundary of forced contact, Mindlin's analysis of contact between spherical surfaces can be used to find shear stress within the contact region due to $\tau_\infty$ as $\xi \to 0$ or $\xi \to 2\Delta$. For simplicity, but without loss of generality, consider the special case of contact between planar bodies with surfaces that each has a constant radius ($R_{1c}$ and $R_{2c}$) at the contact boundary $O_1$ in FIGS. 2A–2C. As shown, one of the surfaces can have zero curvature. The bodies are acted upon by normal and tangential forces $-P$ and T, respectively. In two dimensions, based on Mindlin's results, shear stress ($\sigma_{xy}$) in the contact region ($\theta=0$, $0 \leq r \leq 2\Delta$) can be expressed as (see Hills, D. A., Nowell, D. and Sackfield, A., 1993, "Mechanics of Elastic Contacts", Oxford: Butterworth-Heinemann):

$$\sigma_{xy} = \frac{2\tau_{net}}{\pi}\left[\frac{r}{\Delta}\left(2 - \frac{r}{\Delta}\right)\right]^{-1/2}, \quad (1)$$

where, $\tau_{net}=T/4W\Delta$, in which 2W is thickness in direction normal to the plane, and r is radial distance measured from the contact point. It has been discovered for the present invention that in the limit, as $r \to 0$, $$\sigma_{xy}(r \to 0, \theta = 0) = Q\left(\frac{1}{\sqrt{2\pi r}}\right), \quad (2)$$

where, $$Q = \left(\frac{2\tau_{net}\sqrt{\pi\Delta}}{\pi}\right). \quad (3)$$

As seen in Eq. (2), for a nonzero Q and as $r \to 0$, shear stress is singular. The order of the singularity ($1/\sqrt{r}$) is the same as that associated with a crack in an elastic solid, see Kanninen, M. F. and Popelar, C. H., 1985, "Advanced Fracture Mechanics", Oxford University Press.

Using the two-dimensional (plane stress and plane strain) solution of Hertzian contact, from Hills' "Mechanics of Elastic Contacts" we know $\Delta$ can be expressed as:

$$\Delta = R_c \bar{\sigma}, \quad (4)$$

in which, $R_c$ is 'effective' radius, given by:

$$\frac{1}{R_c} = \frac{1}{R_{1c}} + \frac{1}{R_{2c}}, \quad (5)$$

$$\bar{\sigma} = 4Re\left(\left(\frac{-\sigma_\infty}{\pi \bar{E}}\right)^{1/2}\right), \quad (6)$$

$$\sigma_\infty = \frac{-P}{4WR_c} \quad (7)$$

and $$\bar{E} = \frac{16\mu_1\mu_2}{\mu_1(\kappa_1 + 1) + \mu_2(\kappa_2 + 1)}. \quad (8)$$

In the above, $\mu_i$(i=1,2) is the shear modulus of material i and $\kappa_i$(i=1,2) is defined as:

$\kappa_i=(3-v_i)/(1+v_i)$ in plane stress and $\kappa_i=3-4v_i$ in plane strain, where, $v_i$ is the Poisson's Ratio of material i.

Figure 2:
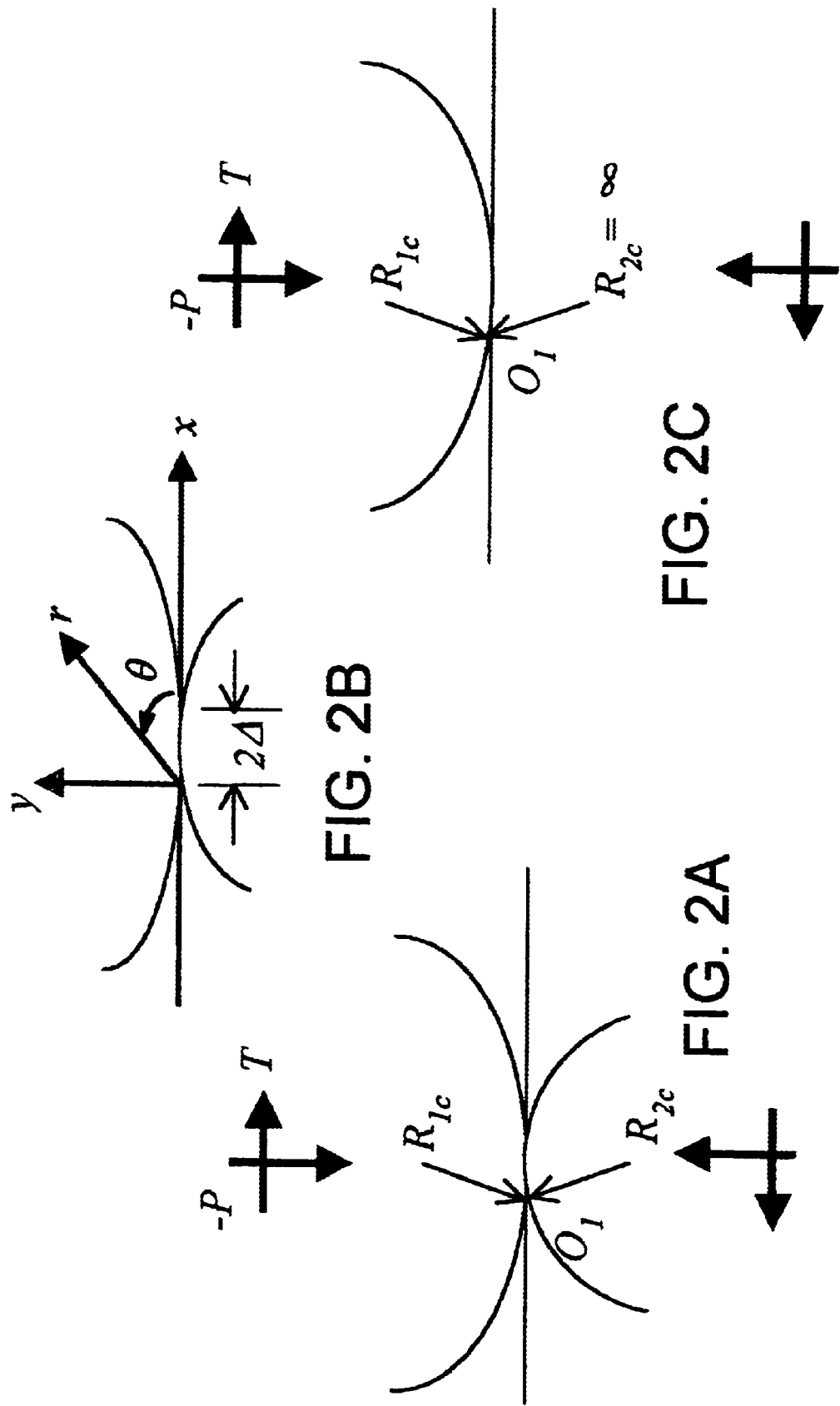
FIGS. 2A–2C shows planar forced contact of surfaces with constant radii and sliding forces.

Substituting eqs. (4) and (6) in eq. (3), the stress intensity factor (Q) for the problems depicted in FIG. 2 is:

$$Q=\tau_{2\infty}\sqrt{\pi\lambda}, \quad (9)$$

where, $$\lambda=4R_c/\pi^2\sigma$$

and $$\tau_\infty = \frac{T}{4WR_c} \quad (10)$$

In eq. (9), Q is reminiscent of the stress intensity factor ($K_{II}$) associated with cracks under Mode II loading.

Figure 3:
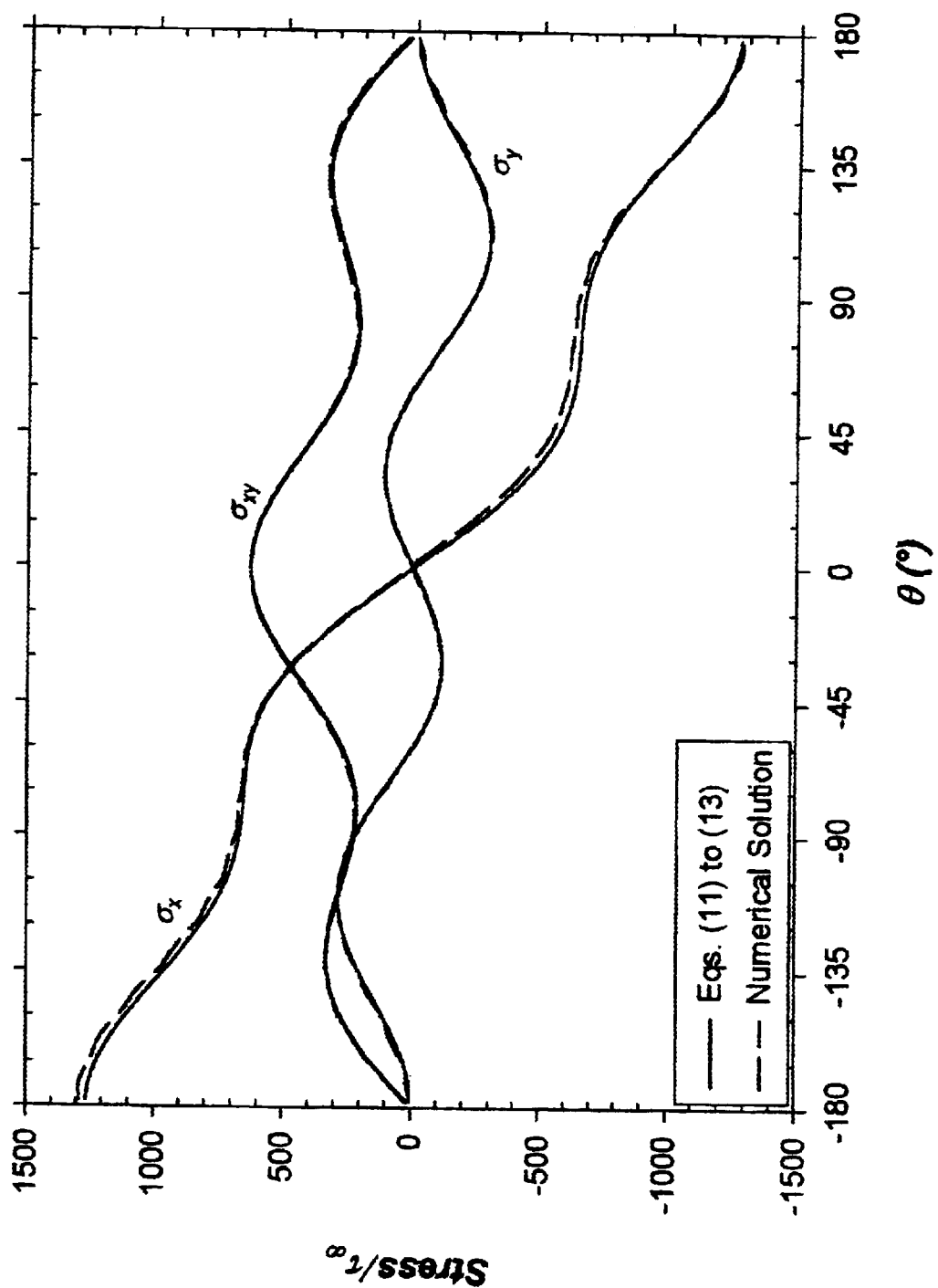
FIG. 3 shows angular distribution of stresses at $r/R_c = 8.8551 \times 10^{-5}$.

The angular distribution of $\sigma_{xy}$(r→0, and θ≠0) is not known in closed form and must be found numerically. For numerical analysis, we use the finite element method to solve the special case of the problem when the materials of the two bodies in contact are the same (i.e., $\mu_1=\mu_2$ and $v_1=v_2$) and the radius of one the bodies is infinite. Details of numerical analysis are given below. FIG. 3 shows the variations of the computed stress components with θ at a small fixed distance from the contact boundary. The figure also shows plots of the asymptotic stress field associated with a Mode II crack, which from Kanninen's "Advanced Fracture Mechanics" is given by:

$$\sigma_{xy}\sqrt{2\pi r} = K_{II}\cos\frac{\theta}{2}\left(1 - \sin\frac{\theta}{2}\sin\frac{3\theta}{2}\right), \quad (11)$$

$$\sigma_{xx}\sqrt{2\pi r} = -K_{II}\sin\frac{\theta}{2}\left(2 + \cos\frac{\theta}{2}\cos\frac{\theta 3}{2}\right), \quad (12)$$

and $$\sigma_{yy}\sqrt{2\pi r} = K_{II}\sin\frac{\theta}{2}\cos\frac{\theta}{2}\cos\frac{3\theta}{2}. \quad (13)$$

For all θ values relevant in the contact problem, the computed stress components for the contact problem and the crack-tip stress components given by eqs. (11) to (13) are in agreement. Together with eq. (2) and eq. (9), results shown in FIG. 3 demonstrate complete analogy between the contact problem and a Mode II crack problem. Thus, Q is analogous to $K_{II}$ and, therefore, for contact problems, $K_{II}$ in eqs. (11), (12) and (13) can be replaced by Q.

Knowing the analogy between Q and $K_{II}$, it becomes possible to exploit well-established theories and methods in fracture mechanics to address a variety of engineering problems involving contact. For example, analogous to fracture mechanics based life prediction methods, Q can be taken to represent propensity for fretting damage. Then, the practical problem of predicting the time of crack nucleation, i.e. crack nucleation life, in structural and machine parts and devices prone to fretting fatigue can be directly addressed. The use of maximum and minimum values ($Q_{max}$ and $Q_{min}$) of the stress intensity factor in predicting crack nucleation life and design improvements is discussed below. The steps leading to such practical applications of the discovery are discussed in below under the heading "Determination of Q Values".

Determination of Q Values

Applicant has discovered that the maximum and minimum values ($Q_{max}$ and $Q_{min}$) of Q can be determined that dictate what the crack nucleation life ($N_i$) would be, of a test specimen or a structural part. The correlation between these Q values and $N_i$ for a specific material combination is established by performing stress analyses of appropriately controlled fretting fatigue tests conducted in the laboratory. For life prediction and design improvement applications, stress analyses of the component are needed to determine $Q_{max}$ and $Q_{min}$ values.

The methods of stress analysis for laboratory tests and the component may be the same or different, depending on the complexity of geometric configurations and loadings involved. A sufficiently general stress analysis method, such as the finite element method (FEM), can be used in the analysis of both the tests and the component. The FEM method is widely used and is available in several commercially available software products such as ANSYS, ABAQUS, NASTRAN, MARC, etc.

The above and other stress analysis methods can be used in the determination of Q values for laboratory tests and for actual engineering components and structures. Determination of Q values from stress analysis results is similar to well-established methods of determining stress intensity factor (K) values in fracture mechanics. One of the most direct methods is to use the computed shear stress ($\sigma_{xy}$) values close to the contact boundary and their relation with Q (see equation (11) and recall that $K_{II}$ can be replaced by Q). For a fixed $\theta=\theta_1$, equation (11) can be used to write the following relation:

$$\text{Log}\sigma_{xy} = \frac{Qf\{\theta_1\}}{\sqrt{2\pi}} - \frac{1}{2}\text{Log} r \text{ for } r \to 0 \quad (14)$$

in which f{$\theta_1$} is given by:

$$f\{\theta_1\} = \cos\frac{\theta_1}{2}\left(1 - \sin\frac{\theta_1}{2}\sin\frac{3\theta_1}{2}\right) \quad (15)$$

It is seen that the relation between Log $\sigma_{xy}$ and Log r is linear (straight line) and the slope of the line is negative ½.

Figure 4:
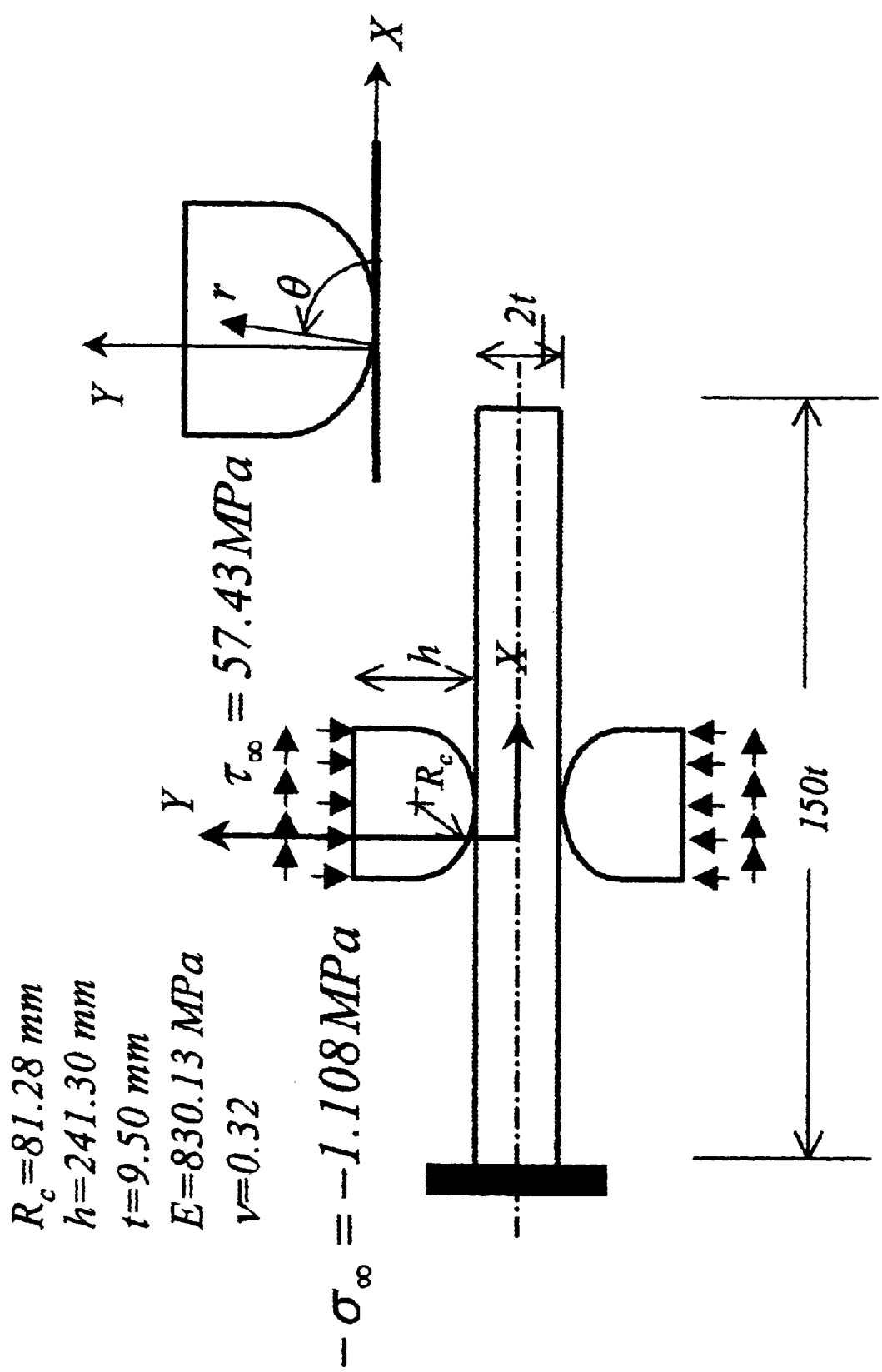
FIG. 4 shows configuration subjected to analysis by FEM.
Figure 5:
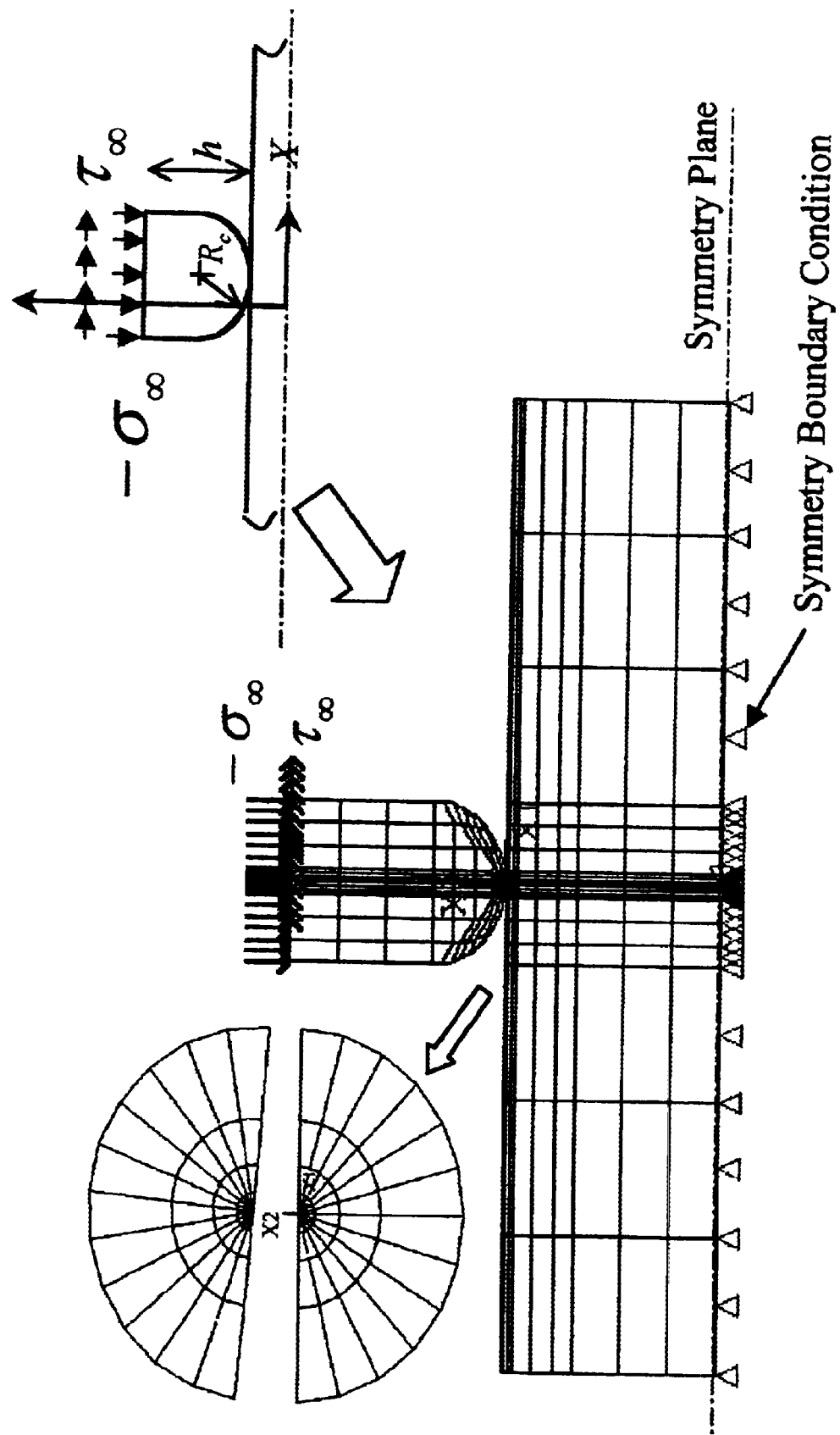
FIG. 5 shows finite element mesh used in analysis.

Equation (14) can be used in determining Q once $\sigma_{xy}$ at some location near the contact point is known. For example, consider the configuration shown in FIG. 4. It involves forced contact between two parts. A finite element mesh used in the analysis of this configuration is shown in FIG. 5. A fine fan-shaped mesh is used around the contact boundary for accurate determination of $\sigma_{xy}$(r) at a fixed value of θ and small values or r. In this example, the mesh is designed such that upon application of loads, the contact point would be at the center of the fan-shaped mesh.

Figure 6:
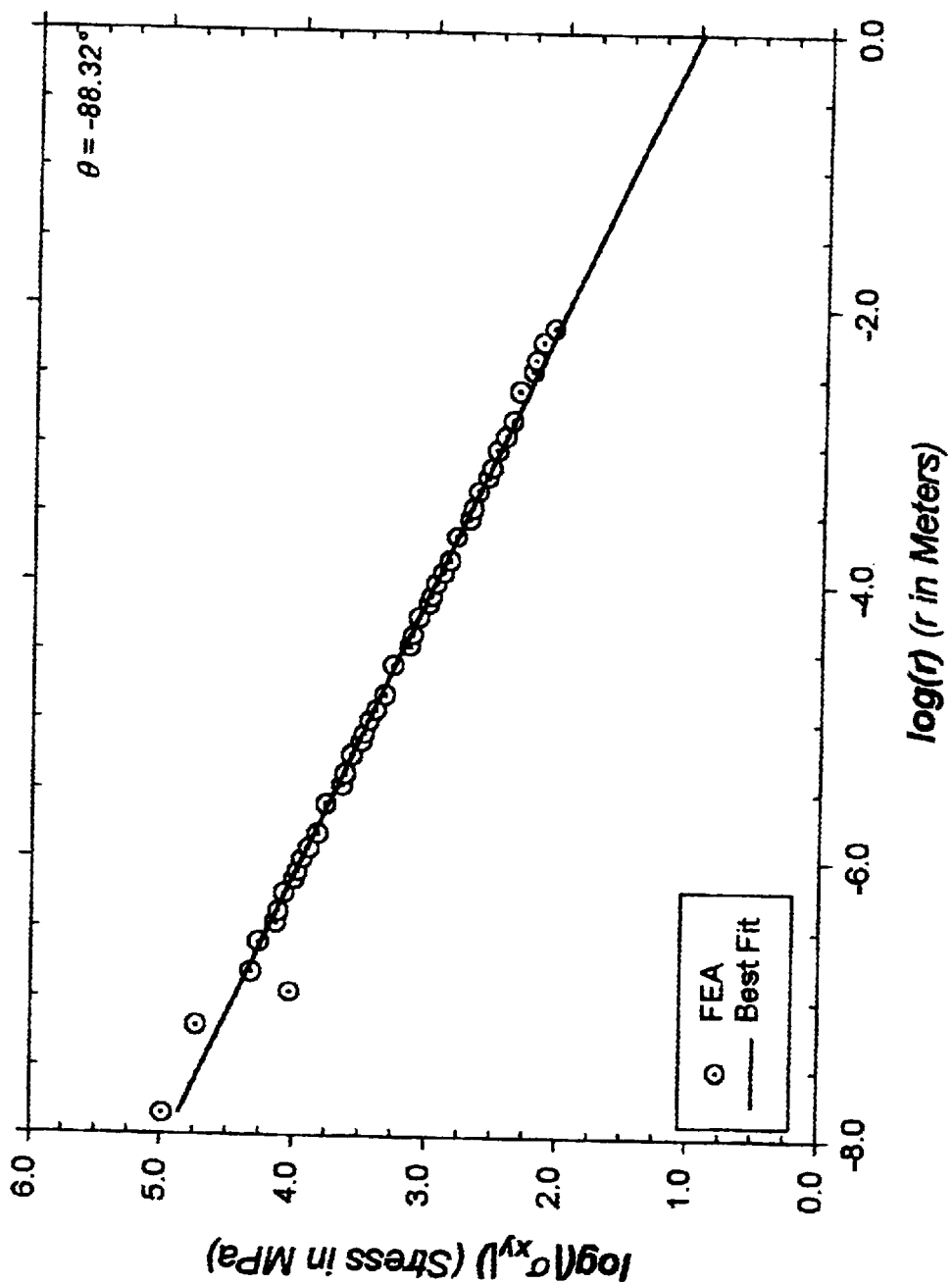
FIG. 6 shows radial distribution of shear stress at $\theta = -88.32°$.

FEM analysis is performed for a prescribed set of elastic properties (elastic modulus and Poisson's Ratio of the materials involved) and loads and boundary conditions appropriate for the test or component, as is commonly done in stress analysis. In the example under consideration, the applied stresses are indicated in FIG. 4 as $\sigma_\infty$ and $\tau_\infty$. The logarithms of the FEM analysis solution of $\sigma_{xy}$ values along a fixed θ are plotted against the logarithm of distance r from the contact point. FIG. 6 shows such a plot at $\theta_1$=–88.32°. As expected, the points in the plot lie on a straight line (within numerical accuracy associated with the FEM method) over a wide range of r values. The deviation from straight line for the smallest r values is due to numerical error and should be ignored (just as in fracture mechanics analyses). The deviation from straight line for large values of r is expected Oust as in fracture mechanics analyses) because equation (14) is valid only for small values of r. As expected, the slope of the straight line in FIG. 6 is negative ½.

The straight line behavior and the slope (negative ½) of the line, shown in FIG. 6, will be the same regardless of the test or the structural component being analyzed. However, the intercept of the straight line with the Log $\sigma_{xy}$ axis will, in general, be different depending on geometry of the structural component being tested and loads. In the example being considered, the intercept is 0.9849. Therefore, using equation (14), $$\frac{Qf\{\theta_1\}}{\sqrt{2\pi}} = 0.9849$$

in which, $f\{\theta_1\}=0.3488$

Therefore, for the example problem, corresponding to the applied loads, Q=7.08 MPa-m$^{1/2}$.

In fretting fatigue tests and in structural components prone to fretting fatigue, the loads fluctuate (i.e., $\sigma_\infty$ and $\tau_\infty$, FIG. 4, will vary). Therefore, one would need to use the above method of determining Q for applied load combinations that result in maximum and minimum values of Q, that is, $Q_{max}$ and $Q_{min}$.

For establishing the correlation between these Q values and $N_i$ for a specific material combination, one would conduct and analyze several fretting tests over a sufficiently wide range of test variables (such as loads, geometric parameters) and plot (for example) the difference $\Delta Q$ between $Q_{max}$ and $Q_{min}$ in each test against measured $N_i$. The plotted points would be delineated into groups having the same R(=$Q_{min}/Q_{max}$) ratio. Such plots would then be used in establishing a relation between a function A{($Q_{max}$, $Q_{min}$} and Log $N_i$ by using appropriate curve-fitting methods.

For life prediction and design improvement applications, one would perform stress analyses of the component to determine $Q_{max}$ and $Q_{min}$ values and A{$Q_{max}$, $Q_{min}$} corresponding to the relevant R-ratio.

Establishment of Relation Between Q Values and Nucleation Life

Recently, Farris, et al., Hutson, et al. and Wallace have reported fretting fatigue life measurements on flat-plate coupons of the titanium alloy Ti-6Al-4V. (See the following references: 1) Farris, T. N., Harish, G., McVeigh, P. A., and Murthy, H., 2000, "Prediction and Observation of Fretting Fatigue of Ti-6Al-4V Subjected to Blade/Disk Type Contacts," Proc. of the 5th National Turbine Engine High Cycle Fatigue (HCF) Conference on CD, Session 13, 11 pages, Chandler, Ariz., March 2000, Published by Universal Technology Corp., Dayton, Ohio; 2) Hutson, A. and Nicholas, T., 1999, "Fretting Fatigue Behavior of Ti-6Al-4V against Ti-6Al-4V under Flat-on-Flat Contact with Blending Radii," Fretting Fatigue-Current Technologies and Practices, ASTM STP 1367, D. W. Hoeppner, V. Chandrasekaran, and C. B. Elliot, Eds., American Society for Testing and Materials, West Conshohocken, Pa., pp. 308–321; 3) Hutson, A. L., Nicholas, T., Olson, S. E. and Ashbaugh, N. E., "Effect of sample thickness on Local contact Behavior in Flat-on Flat Fretting Fatigue Apparatus", submitted to Int. J. of Fatigue, 2001; and 4) Wallace, J. M. and Neu, R. W., "Fretting Fatigue Crack Nucleation in Ti-6Al-4V", 2001, submitted to *Fatigue and Fracture of Engineering Materials and Structures*.)

Farris, Hutson and Wallace all tested the same material (titanium alloy Ti-6Al-4V), but each used significantly different fretting pad configurations and load conditions. Therefore, their measurements are particularly useful in assessing efficacy of $Q_{max}$ and $Q_{min}$ as representing fretting fatigue propensity. To be considered useful, $Q_{max}$ and $Q_{min}$ must have the same relation with nucleation life for a given set of material surfaces, regardless of pad geometry and load conditions.

The test arrangements used by Farris, Hutson and Wallace are shown in FIGS. 7A–7C, respectively. The figures also show the corresponding fretting pad configurations. FIG. 7D shows the length (2L), the width (2W) and the thickness (2t) of a test specimen. In FIGS. 7A and 7B, fretting pads had flat regions (2$c_0$) and rounded ends of radius $R_c$. In FIG. 7C, a "bridge-type" arrangement involving a combination of flat and fixed-radius pads, with $R_c$=50 mm, was used and each pad type consisted of two contact regions. The pad and test specimen dimensions and other test parameters are summarized in Table 1. In FIG. 7C, fretting failure always occurred at a constant radius pads and, therefore, only this pad type is included in Table 1. For each of the five test groups, the table also gives the ratio of minimum to maximum stress (applied stress ratio) corresponding to the oscillatory force T in FIGS. 7A–7C. Each test shown in FIGS. 7A–7C was performed with normal load (–P) held fixed and an oscillatory force of constant amplitude and frequency was applied until specimen failure occurred. The thickness dimension (2t) in FIG. 7B (the Hutson test) was nominally 2.0 mm, but varied somewhat from specimen to specimen.

TABLE 1

Fretting pad and test specimen dimensions in millimeters, normalized pressure ($\sigma$), applied stress-ratio and normalized stress intensity factor (F)

| | Fretting Pad | | | | | | Test Specimen | | |
|---|---|---|---|---|---|---|---|---|---|
| Dimension | Farris | Hutson | | Wallace | | | Ferris | Hutson | Wallace |
| Test Group | (1) | (2) | (3) | (4) | (5) | Dimension | (1) | (2), (3) | (4), (5) |
| $R_c$ | 3.048 | 3.175 | 3.175 | 50.0 | 50.0 | W | 4.7625 | 5.0* | 6.35 |
| $c_0$ | 1.524 | 3.175 | 3.175 | 0.0 | 0.0 | t | 7.70 | 1.0* | 2.50 |
| H | 66.675 | 3.81 | 3.81 | 6.0 | 6.0 | L | 203.2 | 50.0 | 101.50 |
| w | 10.160 | 6.350 | 6.350 | 21.09 | 21.09 | | | | |
| $\sigma$ | 0.0838 to 0.0996 | 0.142 | 0.142 | 0.0073 to 0.142 | | | | | |
| Applied Stress Ratio (R) | –0.068 to 0.497 | 0.1 | 0.5 | 0.1 | 0.5 | | | | |
| F | 0.731 | 0.461 | 0.461 | 1.000 | 1.000 | | | | |

*Nominal values

In Farris and Hutson, the number of cycles at failure (and not at crack nucleation) in each test was recorded. Presently, it is assumed that the numbers approximately represent number of cycles at crack nucleation ($N_i$). Wallace does provide measured values of $N_i$.

Of course, crack nucleation in the test specimens of in each of the above tests can occur without fretting. However, there is substantial experimental evidence that, when fretting is present, it dictates nucleation life (for example, see Wallace's "Fretting Fatigue Crack Nucleation in Ti-6Al-4V" cited above). Therefore, any effect on nucleation life of fatigue without fretting is assumed negligible.

The experimental results in Table 1 offer the opportunity for an assessment of $Q_{max}$ and $Q_{min}$ as representing fretting fatigue propensity. For each fretting pad-specimen combination in Table 1, Q was computed by a finite element analysis discussed below. The reported nominal specimen dimensions were used in all analyses. The computed Q values were normalized by a reference value chosen to be the right hand side of eq. (9). For each case, the normalized value $F(=Q/\tau_\infty\sqrt{\pi/\lambda})$ is given in Table 1. Using this normalization, the F value for a Mindlin problem is unity.

It is likely that there was some variation of sliding force across each pad length, which was not measured in the experiments. In the finite element analyses, uniform sliding traction was prescribed at the top of the pads.

Figure 8A:
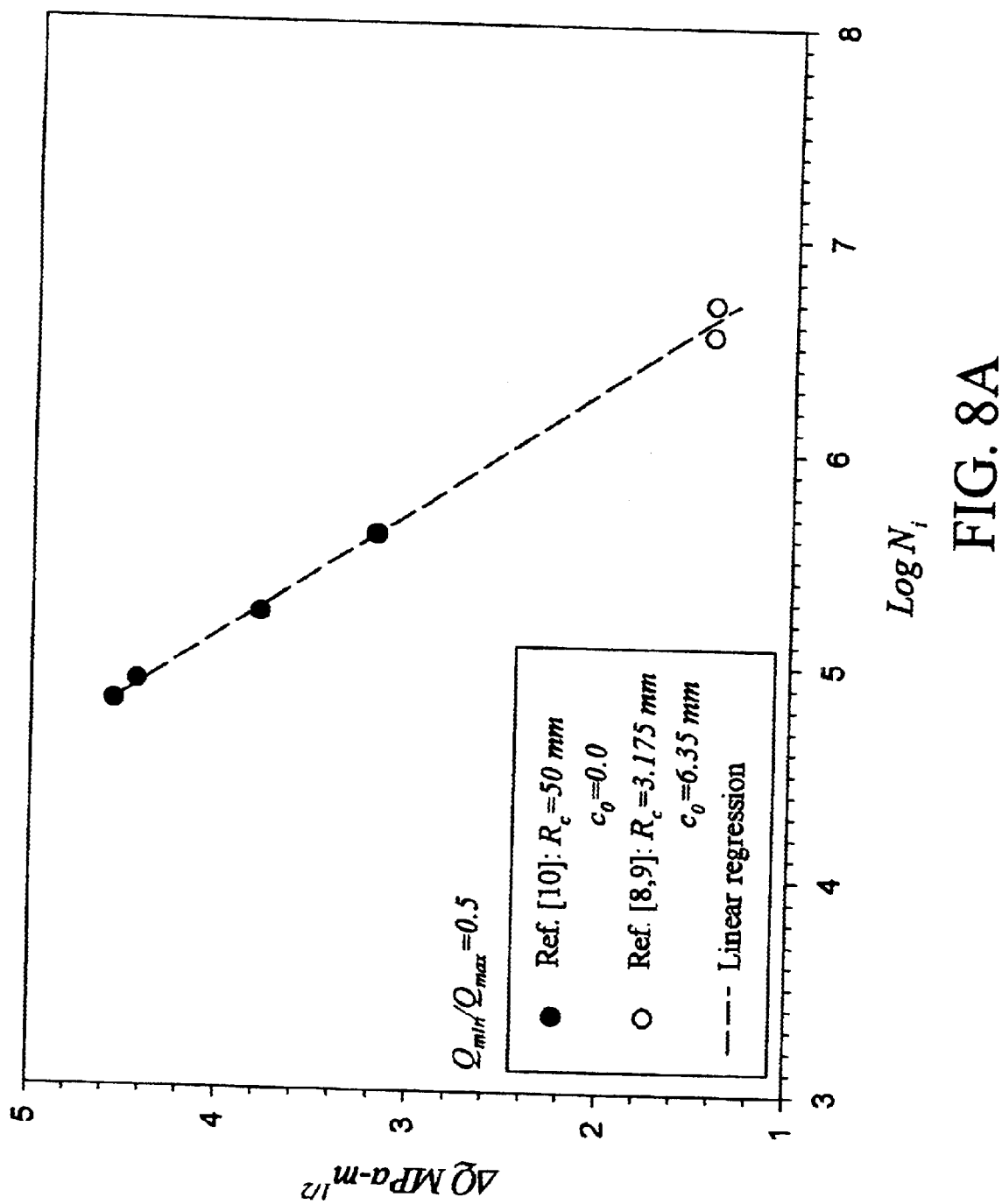
FIG. 8A shows results of analysis of experimental data with R-ratio=0.5.
Figure 8B:
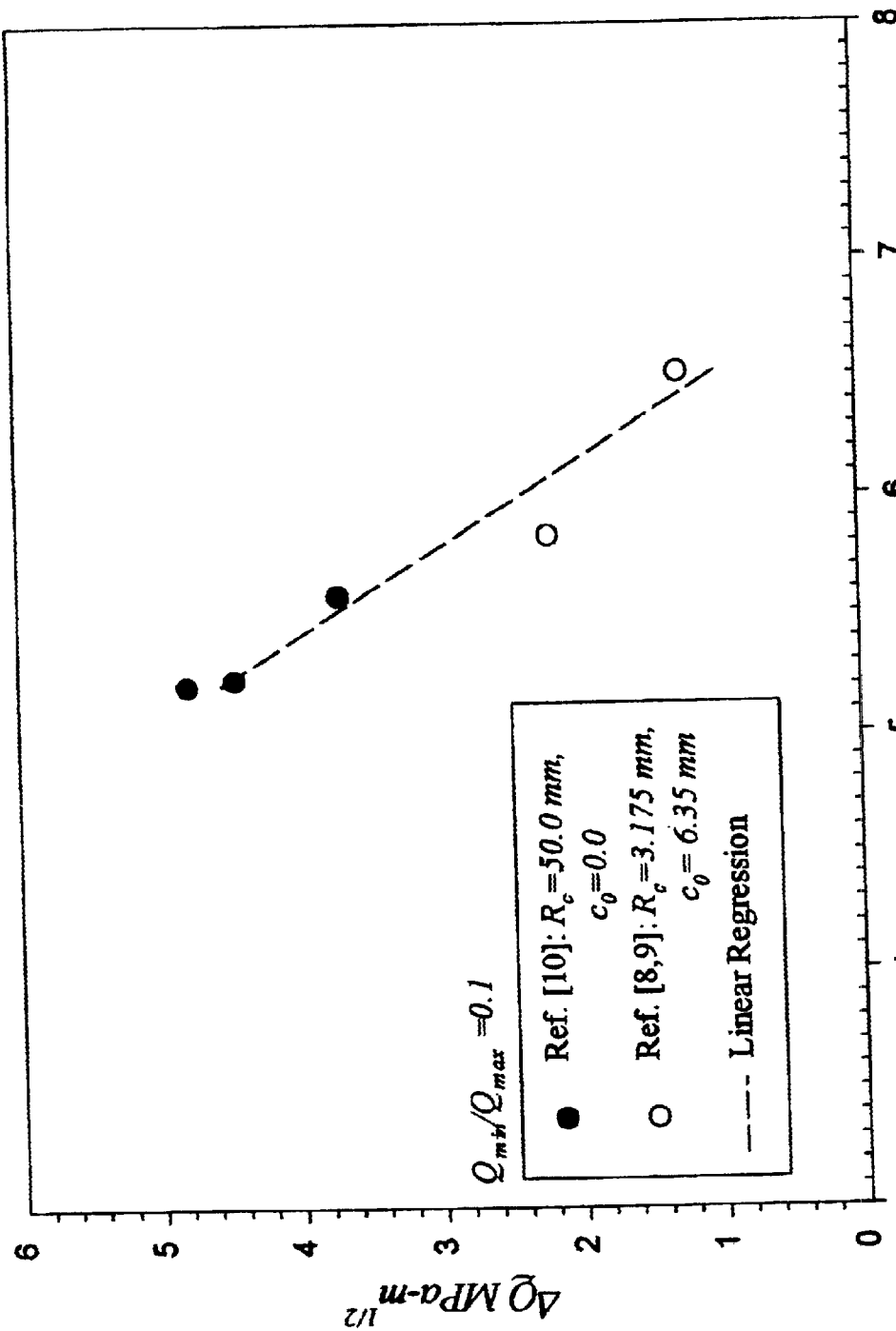
FIG. 8B shows results of analysis of experimental data with R-ratio=0.1.
Figure 8C:
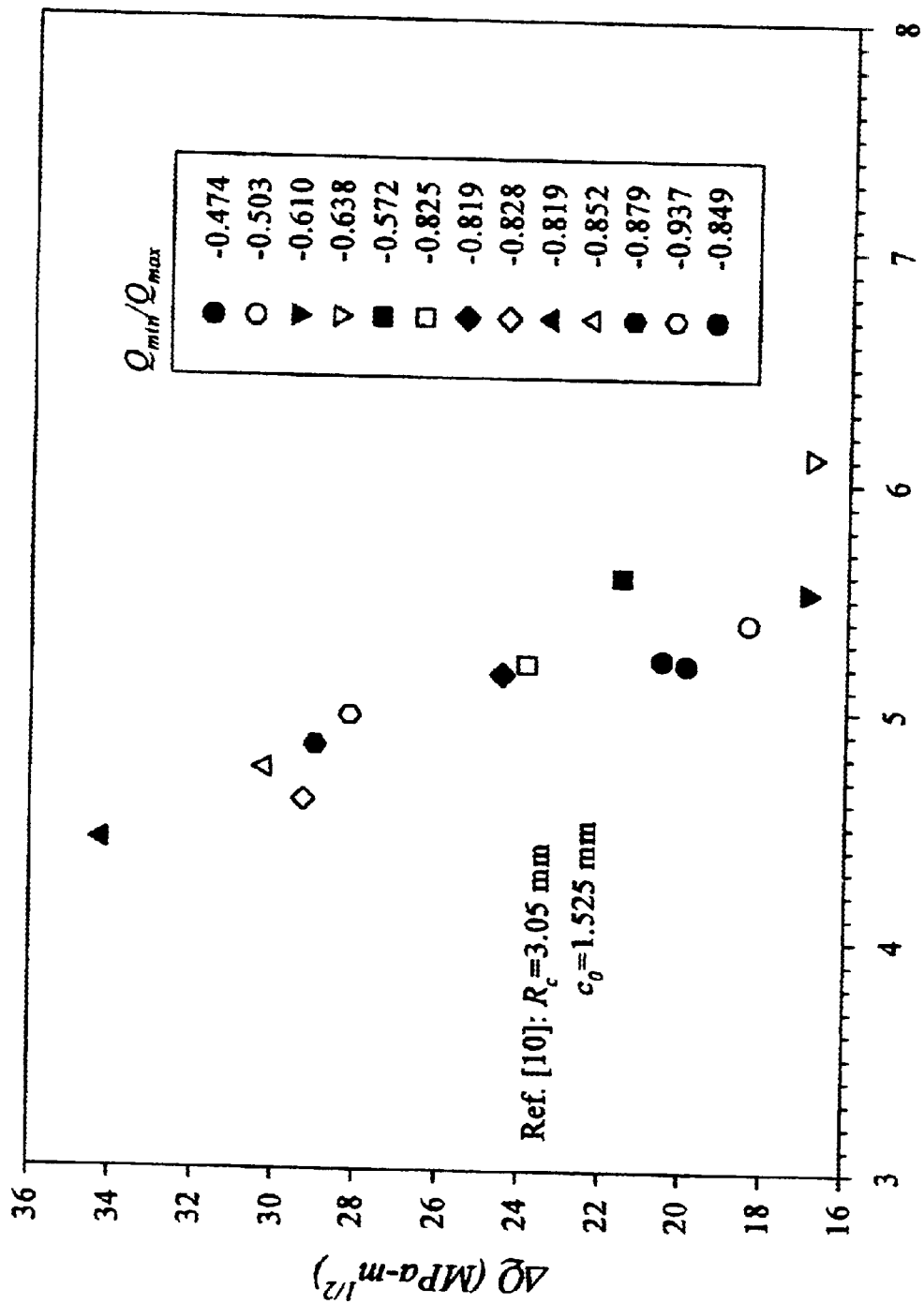
FIG. 8C shows results of analysis of experimental data with multiple R-Ratios.
Figure 8D:
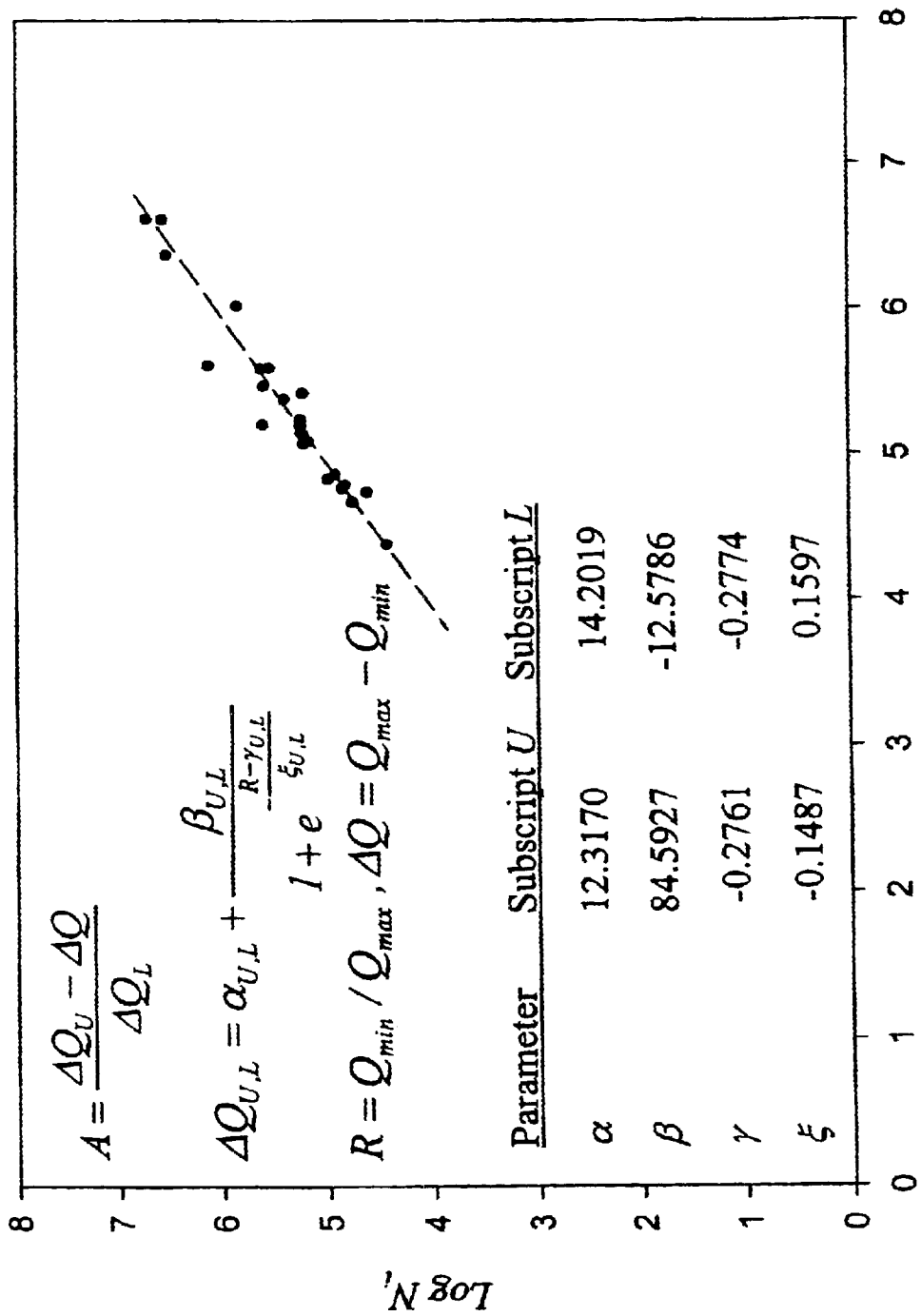
FIG. 8D shows function Log $N_i = A(Q_{max}, Q_{min})$ found by curve-fitting results shown in FIGS. 8A–8C.

Using the F values of Table 1, $Q_{max}$ and $Q_{min}$ during each test were calculated. Plots of $N_i$ vs. $\Delta Q(=Q_{max}-Q_{min})$ for various R-ratios ($R=Q_{min}/Q_{max}$) are shown in FIGS. 8A–8C. Considering that some data scatter is expected in $N_i$ measured in identical tests, there appears to be a correspondence between $N_i$ and $\Delta Q$ for each R-ratio. That is, over significantly wide ranges of load amplitudes and P values, crack nucleation life for a given set of material surfaces can be estimated knowing only $Q_{max}$ and $Q_{min}$. For R=0.1 and R=0.5, this is true regardless of test type and pad geometry. FIG. 8C, showing analysis results of data in from test group 1 correspond to a wide range of negative R-ratios. Test data for negative R-ratios, but using a different test configuration, could not be found in the literature. FIG. 8D shows a functional relation, Log $N_i=A(Q_{max},Q_{min})$, found by curve-fitting the results of FIGS. 8A–8C, to illustrate that $N_i$ for the given set of material surfaces is found knowing only $Q_{min}$ and $Q_{max}$.

Application to Life Prediction and Design Improvement

The discovery that, regardless of geometric configurations involved, $Q_{max}$ and $Q_{min}$ values dictate crack nucleation life under fretting fatigue can be directly applied to life prediction of a variety of engineering components, parts and devices prone to fretting fatigue. Examples include gears, bearings, interconnects in electrical and electronic circuitry, cable-pulley assemblies, riveted and bolted joints in aircraft structures, orthopedic implants and blade-disk joints in turbine engines. Furthermore, the discovery can be directly applied for possible design improvements resulting in longer lives.

Example of Life Prediction

Figure 9:
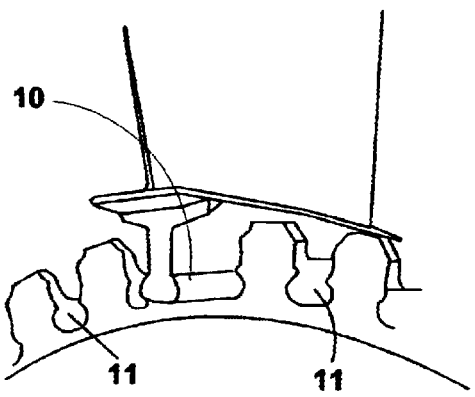
FIG. 9 shows a turbine engine disk with dovetail disk-blade connections.
Figure 10:
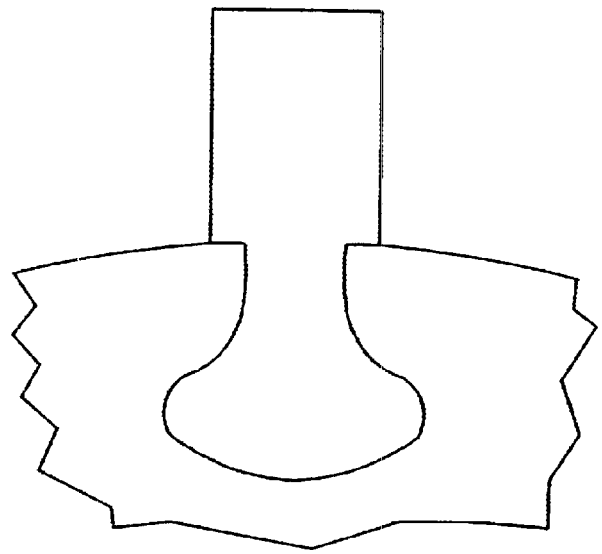
FIG. 10 shows a representative disk-blade joint.

As an example, consider fretting fatigue at the "dovetail" joint between a turbine engine disk and blade. FIG. 9 shows a perspective view of a portion of a turbine engine disk with dovetail disk-blade connections. Fretting fatigue can occur at the blade-disk interface between blade surface 10 and disk surface 11. Assuming that all blades and joints attached to the disc are (nominally) identical and experience the same loading in operation, we can focus on a single representative joint, FIG. 10. Suppose the blade and the disk are of the same material (say, the titanium alloy Ti-6Al-4V) for which an A versus Log $N_i$ relation has already been developed (FIG. 8D). For predicting life of the blade, we need to determine the A value that the blade would experience in service. Once the A value for the blade is determined, we would use the plot shown in FIG. 8D to find the corresponding $N_i$ value, which would be the predicted life. In this example, we are assuming constant amplitude loading in operation. That is, the difference between the maximum and the minimum loads during turbine operation remain the same. Variable amplitude loading can be analyzed, but its consideration would further complicate the example.

Due to rotation of the disk and the resistance offered by the fluid (for example steam in a steam turbine or gas in a gas turbine) to the motion of the blade (FIG. 11), stresses and deformations occur throughout the disk blade assembly. Both the rotational speed and the fluid pressure fluctuate during operation. Generally, these stresses and deformations are calculated (for example, by FEM analyses) and are known to the designer. However, generally, designers do not use sufficiently fine finite element meshes near contact boundaries to allow accurate determination of Q values in the manner described in above.

Figure 11:
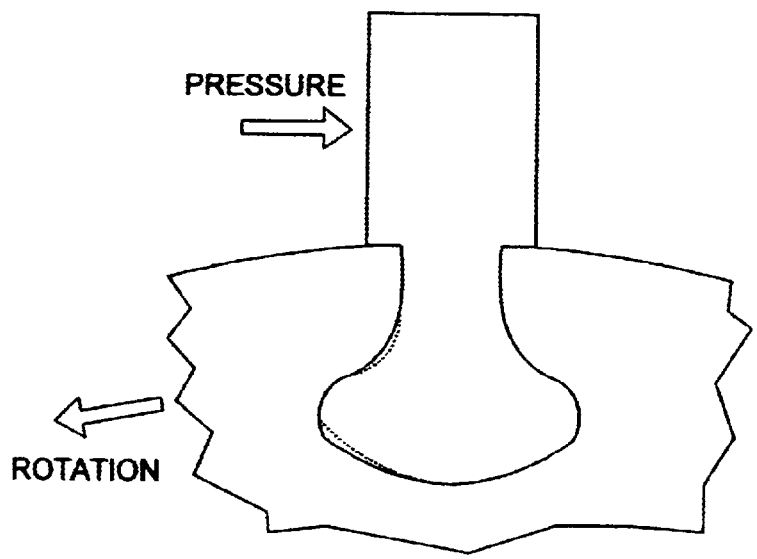
FIG. 11 shows a schematic of disk-blade joint under maximum load.
Figure 12:
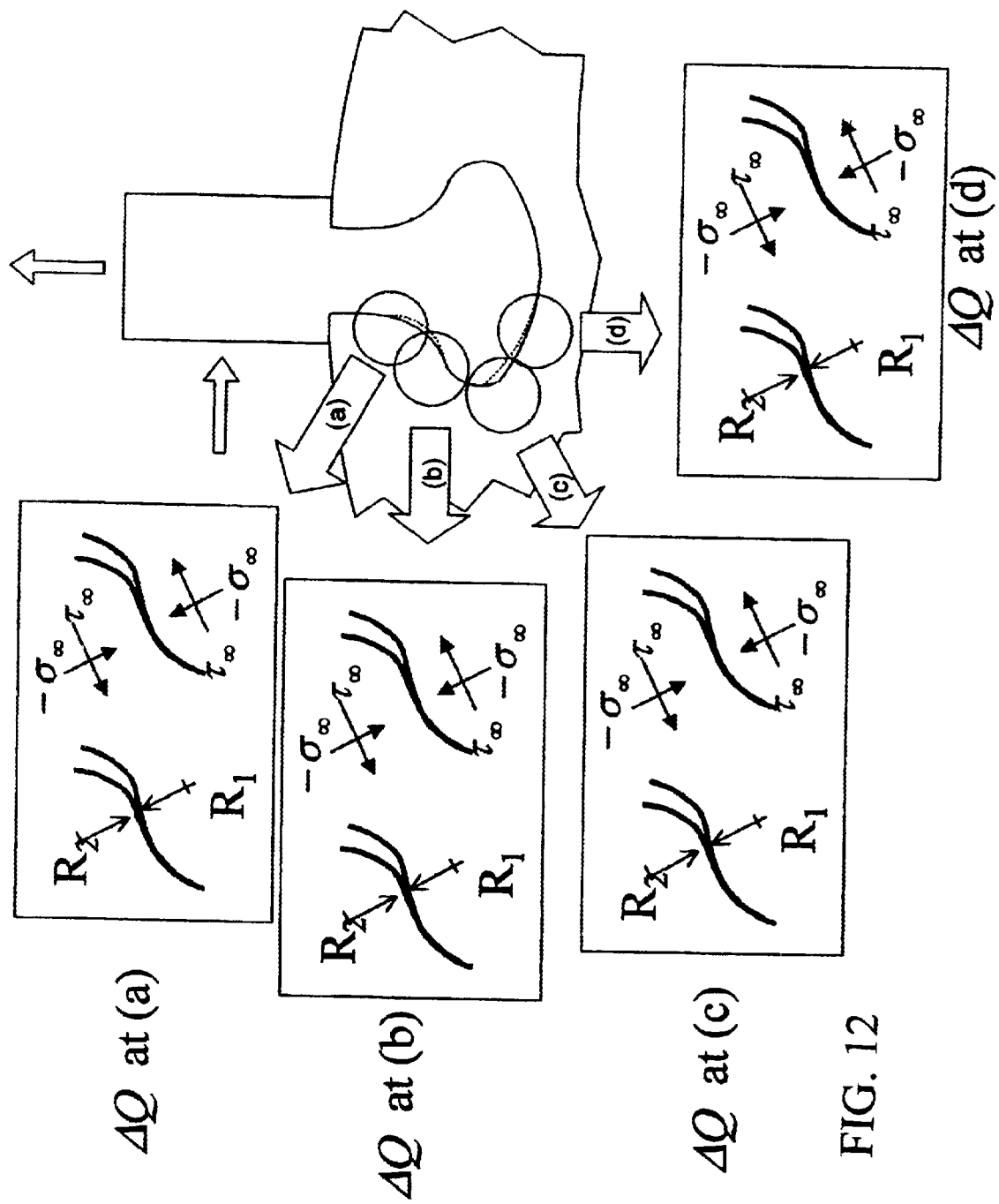
FIG. 12 shows contact boundaries in blade-disk joint.

The dashed lines in FIG. 11 schematically indicate an exaggerated view of deformed shape of the blade-root at maximum operating loads. Four different contact boundaries (a, b, c and d) are shown in FIG. 12, each with its deformed geometry and local normal and shear stresses. Using a refined mesh at each of these contact boundaries (simultaneously in a single FEM analysis, or separately in four different analysis, or using sub-structuring methods commonly used in FEM analyses), the procedure described above can be used to determine maximum and minimum Q values at each of the four locations. Suppose the values found in such a manner are those given in Table 2. A was found using the relation given above under the heading "Establishment of Relation Between Q Values and Nucleation Life" (see FIG. 8D). It is seen that, compared to other locations, $\Delta Q$ is the maximum and A the minimum for location (a). Therefore, crack nucleation life should correspond to this location. Using FIG. 8D, Log $N_i$ is 3.8. Therefore, the predicted life is $10^{3.8}$=6,310 cycles.

TABLE 2

Results of Q value Determination for Blade-Disk Joint

| Location | $Q_{max}$ MPa-m$^{1/2}$ | $Q_{min}$ MPa-m$^{1/2}$ | $Q_{min}/Q_{max}$ (R-Ratio) | $\Delta Q$ MPa-m$^{1/2}$ | A |
|---|---|---|---|---|---|
| (a) | 8.33 | 2.50 | 0.3 | 5.83 | 4.22 |
| (b) | 9.10 | 2.73 | 0.3 | 6.37 | 3.94 |
| (c) | 6.22 | 1.87 | 0.3 | 4.35 | 4.97 |
| (d) | 5.94 | 1.72 | 0.3 | 4.16 | 5.07 |

Example of Design Improvement

Consider that the crack nucleation life of a component, found by life prediction or by actual failure of component, is unacceptably short. A longer life is desired. At least two distinct approaches can be adopted to increase life. These are:

(1) Materials Approach.
(2) Mechanics Approach.

A third approach would involve a combination of the above two approaches.

In the Materials Approach, applied to the example discussed under the heading "Example of Life Prediction", one would seek to replace the blade material with an alternative material offering a higher life at A=3.94. The material change may involve changing only the surface characteristics by, for example, by local heat treatments or application of coatings. After such changes, one would need to perform fretting fatigue tests and analyze the data in the manner described above under the heading "Establishment of Relation Between Q Values and Nucleation Life" unless, of course, if this has already been performed for the changed materials. The goal would be to find material combinations for which Log $N_i$ corresponding to A=3.94 is larger than that for the original alloy (Ti-6Al-4V). Note that in this approach, no attempt is made to change $\Delta Q$ or A values found for location (b) (FIG. 12).

In the Mechanics Approach, the goal is to raise the A value for location (b) so that a desired life is achieved. Suppose the desired life is 100,000 cycles (Log $N_i$=5). From FIG. 8D, the corresponding desired value of A is 5.0 which, for R-ratio of 0.3, corresponds to $\Delta Q$=6.15 MPa-m$^{1/2}$. Achievement of this desired value of A may be approached in several ways. For example, local curvatures of the mating surfaces at location (b) may be repeatedly modified until a desired increase in A is achieved. An overall change in the blade-root shape may be tried to increase the minimum A occurring at any of new contact boundaries thus formed. Local thickness increase in the blade root may provide the desired result. All such attempts would require computations of Q (in the manner described above under the heading "Determination of Q Values") for each new configuration until the desired increase in A is achieved. In some cases it may be possible to use mathematical optimization algorithms to maximize A at any location.

Programmed Computer

Although the calculations and procedures discussed above may be accomplished by hand, in the preferred embodiment a computer is programmed to conduct the analysis. The computer first analyzes the fretting fatigue tests performed on the test specimens to determine Q{N} for the test specimens. Then the computer determines a relationship between Q{N} and crack nucleation ($N_i$) for the test specimens. Data corresponding to tests run on a mechanical device under consideration is then entered into the computer so that Q{N} is determined for the mechanical device under consideration. The computer then corresponds Q{N} for the mechanical device and Q{N} for the test specimens so that crack nucleation ($N_i$) for the mechanical device can be calculated.

While the above description contains many specifications, the reader should not construe these as limitations on the scope of the invention, but merely as exemplifications of preferred embodiments thereof. Therefore, the attached claims and their legal equivalents should determine the scope of the invention.

I claim:

1. A method for determining crack nucleation ($N_i$) for a part subject to fretting fatigue, comprising the steps of:
   A) performing at least one fretting fatigue test on at least one test specimen, wherein said at least one test specimen is comprised of material similar to said part,
   B) analyzing said at least one fretting fatigue test to determine a variation of stress intensity factor as a function of time (Q{N}) for said at least one test specimen,
   C) determining a relationship between said stress intensity factor as a function of time (Q{N}) and said crack nucleation ($N_i$) for said at least one test specimen, and
   D) determining a variation of stress intensity factor as a function of time (Q{N}) for said part under operating conditions and loads of said part,
   E) corresponding said variation of stress intensity factor as a function of time (Q{N}) for said part to said variation of stress intensity factor as a function of time (Q{N}) for said at least one test specimen to determine a crack nucleation ($N_i$) for said part.

2. The method as in claim 1, wherein said at least one fretting fatigue test is a plurality of fretting fatigue tests and said at least one test specimen is a plurality of test specimens.

3. The method as in claim 1, wherein said operating loads and conditions are projected operating loads and conditions.

4. The method as in claim 1, wherein said operating loads and conditions are actual operating loads and conditions.

5. The method as in claim 1, wherein said at least one test specimen is comprised of material identical to said part.

6. The method as in claim 1, wherein said crack nucleation ($N_i$) for said at least one test specimen is specimen failure ($N_f$).

7. The method as in claim 1, wherein said analyzing said at least one fretting fatigue test to determine a variation of stress intensity factor as a function of time (Q{N}) for said at least one test specimen is accomplished utilizing a closed form procedure.

8. The method as in claim 1, wherein said analyzing said at least one fretting fatigue test to determine a variation of stress intensity factor as a function of time (Q{N}) for said at least one test specimen is accomplished utilizing a numerical mathematical procedure.

9. The method as in claim 8, wherein said numerical mathematical procedure is the finite element method.

10. The method as in claim 1, wherein said determining a variation of stress intensity factor as a function of time (Q{N}) for said part under the operating conditions and loads of said part is accomplished utilizing a closed form procedure.

11. The method as in claim 1, wherein said determining a variation of stress intensity factor as a function of time (Q{N}) for said part under the operating conditions and loads of said part is accomplished utilizing a numerical mathematical procedure.

12. The method as in claim 11, wherein said numerical mathematical procedure is the finite element method.

13. The method as in claim 1, further comprising the step of modifying the design of said part to extend said crack nucleation ($N_i$) for said part and then repeating said steps as necessary until a desired crack nucleation ($N_i$) for said part is achieved.

14. The method as in claim 1, further comprising the step of modifying the material composition of said part to extend said crack nucleation ($N_i$) for said part and then repeating said steps as necessary until a desired crack nucleation ($N_i$) for said part is achieved.

15. The method as in claim 1, further comprising the step of modifying the surface characteristics of said part to extend said crack nucleation ($N_i$) for said part and then repeating said steps as necessary until a desired crack nucleation ($N_i$) for said part is achieved.

16. The method as in claim 1, further comprising the step of modifying the material composition and the design of said part to extend said crack nucleation ($N_i$) for said part and then repeating said steps as necessary until a desired crack nucleation ($N_i$) for said part is achieved.

17. The computer as in claim 16, wherein said determining a variation of stress intensity factor as a function of time (Q{N}) for said part under the operating conditions and loads of said part is accomplished utilizing a closed form procedure.

18. The computer as in claim 16, wherein said determining a variation of stress intensity factor as a function of time (Q{N}) for said part under the operating conditions and loads of said part is accomplished utilizing a numerical mathematical procedure.

19. The computer as in claim 18, wherein said numerical mathematical procedure is the finite element method.

20. A computer system for determining crack nucleation ($N_i$) in a part subject to fretting fatigue, comprising:
   A) a computer processor, and
   B) a memory unit connected to said processor and storing a program for controlling the operation of said processor, said processor operative with said program in said memory to:
      1) analyze the results of at least one fretting fatigue test to determine the variation of stress intensity factor as a function of time (Q{N}) for at least one test specimen, wherein said at least one fretting fatigue test was performed on at least one test specimen, wherein said at least one test specimen is comprised of material similar to said part,
      2) determine a relationship between said stress intensity factor as a function of time (Q{N}) and said crack nucleation ($N_i$) for said at least one test specimen,
      3) determine a variation of stress intensity factor as a function of time (Q{N}) for said part under the operating conditions and loads of said part, and
      4) correspond said variation of stress intensity factor as a function of time (Q{N}) for said part to said variation of stress intensity factor as a function of time (Q{N}) for said at least one test specimen to determine a crack nucleation ($N_i$) for said part.

21. The computer as in claim 20, wherein said at least one fretting fatigue test is a plurality of fretting fatigue tests and said at least one test specimen is a plurality of test specimens.

22. The computer as in claim 20, wherein said operating loads and conditions are anticipated operating loads and conditions.

23. The computer as in claim 20, wherein said operating loads and conditions are actual operating loads and conditions.

24. The computer as in claim 20, wherein said at least one test specimen is comprised of material identical to said part.

25. The computer as in claim 20, wherein said crack nucleation ($N_i$) for said at least one test specimen is specimen failure ($N_f$).

26. The computer as in claim 20, wherein said analyzing said at least one fretting fatigue test to determine a variation of stress intensity factor as a function of time (Q{N}) for said at least one test specimen is accomplished utilizing a closed form procedure.

27. The computer as in claim 20, wherein said analyzing said at least one fretting fatigue test to determine a variation of stress intensity factor as a function of time (Q{N}) for said at least one test specimen is accomplished utilizing a numerical mathematical procedure.

28. The method as in claim 27, wherein said numerical mathematical procedure is the finite element method.

* * * * *